US00PP33293P2

(12) United States Plant Patent
Hansen

(10) Patent No.: US PP33,293 P2
(45) Date of Patent: Jul. 27, 2021

(54) ***DIANTHUS* PLANT NAMED 'PAINT THE TOWN RED'**

(50) Latin Name: ***Dianthus* hybrid**
Varietal Denomination: Paint the Town Red

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,291

(22) Filed: Dec. 18, 2020

(51) Int. Cl.
*A01H 5/02* (2018.01)
*A01H 6/30* (2018.01)

(52) U.S. Cl.
USPC ..... Plt./277

(58) Field of Classification Search
USPC ..... Plt./277, 278, 273
CPC ..... A01H 5/02; A01H 5/0233; A01H 5/00; A01H 6/30; A01H 6/305; A01H 6/1424
See application file for complete search history.

*Primary Examiner* — June Hwu

(57) ABSTRACT

A new and unique plant cultivar of perennial carnation or pinks, *Dianthus* plant named 'Paint the Town Red' with numerous, single, lightly-spicy fragrant flowers producing a full rounded face. Each flower has five overlapping petals that are deep magenta-red colored without darker red bars in the center. Petals have moderately coarse dentate apices. Flowering season is strong for four weeks beginning in late spring and continues to mid-fall. The habit is compact and dense with glaucous blue-green foliage.

1 Drawing Sheet

Botanical denomination: *Dianthus* hybrid.
Cultivar designation: 'Paint the Town Red'.

STATEMENT REGARDING PRIOR DISCLOSURES UNDER 37 CFR 1.77(B)(6)

The first non-enabling disclosure of the claimed plant was made by Walters Gardens, Inc. on Dec. 1, 2019 in the form of a website brief description and photograph followed by a short description and photograph in the "Walters Gardens 20-21 Catalog" by Walters Gardens, Inc. The first sales of the claimed plant was on Jun. 29, 2020 by Walters Gardens, Inc. to Walla Walla Nursery Co. Walters Gardens, Inc. obtained the new plant and information about the new plant directly from the inventor. No plants of *Dianthus* 'Paint the Town Red' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of carnation or pinks from the genus *Dianthus* and given the cultivar name 'Paint the Town Red'. The new plant was the result of an intentional cross on Jun. 14, 2012 under the direction of the inventor between 'Neon Star' U.S. Plant Pat. No. 14,549 as the female or seed parent and 'Kahori' (not patented) as the male or pollen parent. The cross was harvested and sown in the fall of 2012. The new hybrid was first selected from trials at a wholesale perennial nursery in Zeeland, Mich. during the summer of 2014 as a single seedling clone and given the breeder code number 12-94-1 later in the evaluation processes. *Dianthus* 'Paint the Town Red' has been asexually propagated at the same nursery in Zeeland, Mich. since 2014 using traditional shoot tip cutting procedures and later sterile shoot-tip tissue culture and found to reproduce plants that are identical and exhibit all the characteristics of the original plant in successive generations.

SUMMARY OF THE INVENTION

*Dianthus* 'Paint the Town Red' has not been evaluated under all possible environmental conditions. The phenotype may vary with variations in environment including: growing temperature, available sunlight, nutrients, water, etc. without a change in the genotype of the plant.

The closest comparison plants to the new plant known to the inventor include: 'Paint the Town Magenta' U.S. Plant Pat. No. 29,922, 'Paint the Town Fuchsia' U.S. Plant Pat. No. 28,636, 'Kahori' (not patented) and 'Paint the Town Red' copending U.S. Plant Patent Application.

'Paint the Town Magenta' has a similar habit and foliage but the flowers are slightly smaller and of vibrant magenta-pink. 'Paint the Town Fuchsia' has similar habit and foliage, but the flowers are slightly smaller and fuchsia colored with lavender centers. 'Paint the Town Fancy' has similar habit and foliage and the flowers are more rosy-fuchsia colored with a larger dark red bar. 'Neon Star' (in side by side growing conditions of mature plants) has a larger habit and flowers that are lighter pink with a lighter lavender-pink bar. The male parent, KAHORI®, has smaller habit with more light green foliage and the flowers are more pinkish.

*Dianthus* 'Paint the Town Red' is distinct from its parents and all other *Dianthus* known to the applicant in the following combined traits:

1. Single flowers with a five overlapping petals forming a full rounded face;
2. Petals have moderately-coarse dentate apices;
3. Petal color is a deep magenta red;

4. Numerous flowers per plant on heavily branched upright stems;
5. Prolonged flowering period with a strong flush in late spring and continuing to mid- fall;
6. Compact habit and dense, glaucous, blue-green foliage.

BRIEF DESCRIPTION OF THE DRAWINGS

The photographs of 'Paint the Town Red' are of a two-year-old plant grown in full-sun trial garden in Zeeland, Mich. showing the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
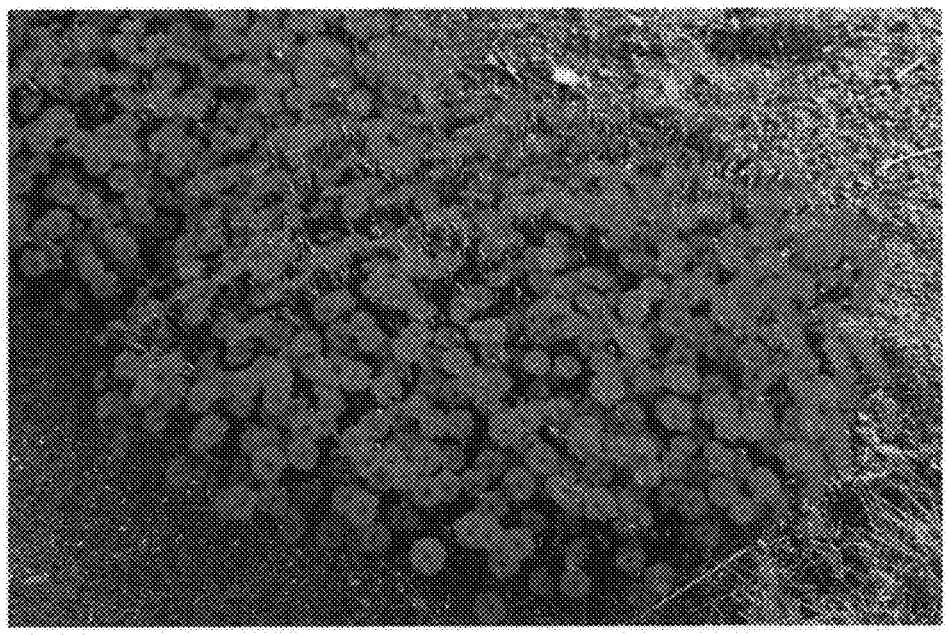
FIG. 1 shows the habit of the plant in mid-season flowering.
Figure 2:
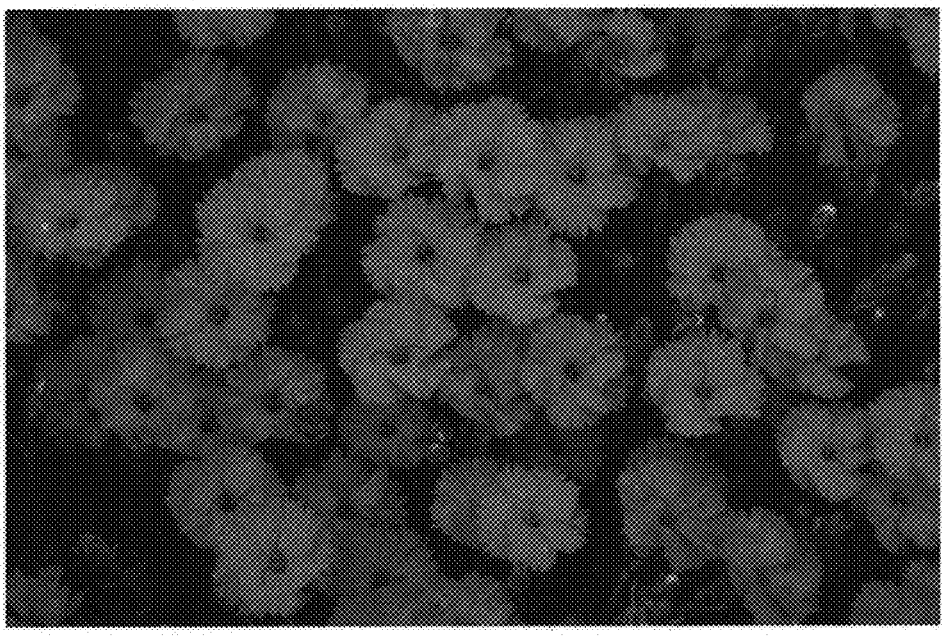
FIG. 2 shows a close-up of the flowers and buds.

The following detailed description of 'Paint the Town Red' is based on observations of two-year-old plants in a full-sun trial garden at a nursery in Zeeland, Mich. with supplemental watering, light additions of fertilizer and free of other plant growth regulators. All color usage is in accordance with the 2015 edition of The Royal Horticultural Colour Chart except where common dictionary terms are used.

Botanical classification: *Dianthus* hybrid;

Parentage: The female or seed parent is 'Neon Star'; the male or pollen parent is KAHORI®;

Plant habit: Caespitose, herbaceous, evergreen, winter-hardy perennial; stems and peduncles highly branched, mostly erect stems to slightly arching; height of foliage about 11.5 cm and about 30.0 cm across; height in flower is about 15.0 cm;

*Root system*.—Fine, fibrous; color nearest RHS 155D.

*Vigor*.—Good, spring planted plugs finish in 3.8 liter pots in seven to eight weeks.

Foliage:

*Leaf type*.—Simple, linear, opposite, decussate, sessile, glabrous, strongly glaucous both adaxial and abaxial; margin entire to micro-serrulate; apex narrowly acute; base truncate, decurrent, clasping; straight; no fragrance detected.

*Leaf dimensions*.—To about 32.0 mm long and about 3.5 mm wide near middle, average about 29.0 cm long and 3.2 mm wide.

*Leaf color*.—Young expanding and mature leaves adaxial and abaxial blend nearest RHS N138B.

*Venation*.—Not pronounced; obscurely pinnate, coloration same as that of leaf top and bottom.

Stems: About 100 per plant; upright; cylindrical, hollow; glabrous; glaucous; branching in upper nodes;

*Stem size*.—About 10.0 cm long to peduncle and about 2.5 mm wide at base.

*Stem color*.—Between RHS N187B and RHS N187C.

*Branching*.—Numerous; typically alternate from lower nodes; about 12 per main stem and about 200 per plant in late spring peak; branch size average about 3.5 cm long and 1.0 mm diameter at time of initial flowering.

*Nodes*.—About 4.0 mm across; between RHS N187B and RHS N187C.

*Internodes*.—About 10 to 12 per stem before peduncle; average about 1.2 cm apart depending on growing temperature, shorter in cooler conditions.

*Inflorescence*.—Flowering in the upper 4.5 cm and to about 7.2 cm across; with an average of 2.4 flowers per inflorescence.

*Flower bud*.—Slowly opening; glabrous; glaucous; with calyx still closed: cylindrical with attenuate base and rounded apex; about 23.0 mm long and 4.0 mm across; without extrusion of style.

*Flower bud color*.—With petals extended beyond calyx petal portion nearest RHS 61A; calyx nearest RHS 138A.

Flower:

*Type*.—Terminal, cymose; perfect; salverform; actinomorphic; single.

*Attitude*.—Upright to slightly outwardly around perimeter of plant.

*Dimension*.—About 2.6 cm across and extending about 2.8 cm above base of calyx tube and 4.5 mm wide at apex of calyx.

*Flowers per stem*.—Typically 2 to 4, average 2.4.

*Pedicel*.—Glaucous, glabrous, cylindrical, stiff; primarily upright; short.

*Pedicel size*.—To about 20.0 mm long and about 1.5 mm diameter.

*Pedicel color*.—Between RHS 146D and RHS 137D.

*Flower period*.—Beginning mid-May with a strong flush for about four weeks and continuing more sparsely through mid-fall.

*Flower fragrance*.—Lightly spicy.

*Flower lasting quality*.—Individually about seven to ten days on or cut from plant.

*Corolla profile*.—Lower part flat; upper portion flat to slightly convex.

*Petals*.—Five; glabrous adaxial and abaxial except basal 5.0 mm of adaxial limb puberulent; consisting of a rounded limb and a claw; limb trapezoidal and limb and claw combined are flabellate; limb apex and margin moderately-coarse dentate with many incisions or teeth to about 2.0 mm long and 2.0 mm wide at base; limb base attenuate toward claw; claw base attenuate; bent outwardly at limb base creating a flat rounded face; persistent; darker eye band or spots.

*Petal dimensions*.—Limb to about 10.0 mm long and 14.0 mm wide; claw about 18.0 mm long and 4.5 mm wide tapering to attenuate base of about 1.0 mm across; whole petal to about 28.0 mm long, average about 27.0 mm long.

*Petal color*.—Young adaxial claw base nearest RHS NN155B and distally nearest RHS 145D, young adaxial limb between RHS 61A and RHS N66A without darker bar near eye; young abaxial claw nearest RHS 145D in distal 13 mm, in basal 2.0 mm portion between RHS 61B and RHS 61C, young abaxial limb nearest RHS 61A; mature adaxial claw between RHS 145D and RHS NN 155D in proximal 12 mm and nearest RHS 70C in distal 3 mm transitioning to limb, mature adaxial limb nearest RHS 61A; mature abaxial claw nearest RHS 145D in proximal 13 mm and distal 2 mm nearest RHS 61B, mature abaxial limb nearest RHS 60B.

*Calyx*.—Tubular; to about 16.0 mm long and 5.0 mm diameter near center.

*Sepals*.—Five; linear; acute apex and fused in basal 12.0 mm forming five-toothed calyx tube; glabrous adaxial and abaxial; glaucous abaxial; margins entire to micro-ciliolate.

*Sepal size*.—Individually about 16.0 mm long and to about 3.0 mm across at fusion.

*Sepal color*.—Adaxial nearest RHS 146D; abaxial nearest RHS 138A.

*Peduncle*.—Glabrous; glaucous; hollow, cylindrical; stiff; about 4.5 cm long and about 1.0 mm diameter at base; attitude mostly upright to slightly arching.

*Peduncle color*.—Variable, nearest RHS 137D and RHS 146D.

*Epicalyx*.—Two pairs subtending each flower; both pairs adpressed; opposite, glaucous, glabrous; sessile, margin entire; ovate; inner pair narrowly acute apex and truncate base, 9.0 mm long and about 3.5 mm across near middle; outer pair with very short narrowly acute apex, truncate clasping base, about 9.0 mm long and about 4.5 mm wide.

*Epicalyx color*.—Both pairs variable; adaxial and abaxial with translucent 1.0 mm wide margin nearest RHS 155A and remaining middle to apex nearest RHS 137B; no anthocyanin pigment noted.

*Androecium*.—Up to 10; not fully developed. Filaments: straight to about 7 mm long and 0.1 mm diameter, average 5 mm long and 0.1 mm diameter; color nearest RHS NN155A. Anther: rudimentary or not observed; oblong; basifixed; about 0.5 mm long and 0.2 mm diameter; color nearest RHS 160C. Pollen: not observed.

*Gynoecium*.—Single; to about 29.0 mm long. Style: bifurcate just above ovary; shoulder absent; to 20.0 mm long and 1.0 mm across; color on young flower nearest RHS NN155D, mature flower proximally nearest RHS NN155D and distally between RHS 187C and RHS 61A, hairs proximally nearest RHS 61A and distally nearest RHS 187C. Stigma: slightly flattened abaxial to adaxial; puberulent along adaxial surface; about 1.0 mm long and 0.7 mm wide; color nearest RHS 187C. Ovary: superior; cylindrical; rounded apex and truncate to slightly tapering base; smooth, lustrous; about 9.0 mm long and 4.0 mm diameter; color on young flower nearest RHS 150C, mature distally nearest RHS 144A and proximally nearest RHS 144B.

Fruit and seed: Not observed;

Disease resistance: The new plant is resistance to center die out from fungus or high temperatures. The plant grows best with adequate moisture and well-drained soil, but is able to tolerate some drought once established. Hardiness at least from USDA zone 4 through zone 9.

It is claimed:

1. A new and distinct *Dianthus* plant named 'Paint the Town Red' essentially as herein described and illustrated.

* * * * *